United States Patent
Widlund et al.

[11] Patent Number: 5,814,034
[45] Date of Patent: Sep. 29, 1998

[54] METHOD FOR THE MANUFACTURING OF AN ABSORBENT STRUCTURE AND AN ABSORBENT ARTICLE

[75] Inventors: Urban Widlund, Mölnlycke; Eje Österdahl, Västra; Roy Hansson, Mölndal; Milan Kolar, Sundsvall, all of Sweden

[73] Assignee: Mölnlycke AB, Göteborg, Sweden

[21] Appl. No.: 436,271

[22] PCT Filed: Nov. 15, 1993

[86] PCT No.: PCT/SE93/00973

§ 371 Date: Aug. 2, 1995

§ 102(e) Date: Aug. 2, 1995

[87] PCT Pub. No.: WO94/10955

PCT Pub. Date: May 26, 1994

[30] Foreign Application Priority Data

Nov. 17, 1992 [SE] Sweden .................................. 9203445

[51] Int. Cl.⁶ .............................. A61F 13/15; D01G 25/00
[52] U.S. Cl. ........................ 604/367; 604/375; 604/378; 604/379; 19/296
[58] Field of Search ..................................... 604/367, 374, 604/375, 378, 379, 385.1; 156/62.2; 425/80.1–82.1, 84; 428/224; 19/296

[56] References Cited

U.S. PATENT DOCUMENTS

| 4,507,122 | 3/1985 | Levesque . |
| 4,610,678 | 9/1986 | Weisman et al. ....................... 604/368 |
| 5,134,007 | 7/1992 | Reising et al. ........................ 604/385.1 |
| 5,324,575 | 6/1994 | Sultze et al. ............................ 428/224 |

FOREIGN PATENT DOCUMENTS

| 0202472A1 | 11/1986 | European Pat. Off. . |
| 0251675A2 | 1/1988 | European Pat. Off. . |
| 0255654A1 | 2/1988 | European Pat. Off. . |
| 0360472A2 | 3/1990 | European Pat. Off. . |
| 0523744A1 | 1/1993 | European Pat. Off. . |
| 468744 | 3/1993 | Sweden . |
| 2140471 | 11/1984 | United Kingdom . |
| 9005808 | 5/1990 | WIPO . |
| WO 90/05808 | 5/1990 | WIPO . |
| 9111162 | 8/1991 | WIPO . |

*Primary Examiner*—John G. Weiss
*Assistant Examiner*—David J. Cho
*Attorney, Agent, or Firm*—Burns, Doane, Swecker & Mathis, L.L.P.

[57] ABSTRACT

A method for the manufacturing of an absorbent structure in an absorbent article, such as a sanitary napkin, tampon, panty protector, wound or sore dressing and like articles is produced by using absorbent material in roll form directly in the product without first defibrating the material and then forming a mat. The material possesses good dispersion properties and swelling properties, which are meaningful to the function of the product. A high surface dryness is obtained, among other things. In addition to cellulose fibers, the absorbent structure may also include superabsorbent material and/or binding fibers, among other ingredients. The pulp mat is very thin, therewith obviating the need to compress the mat further in the product. In the case of certain product applications, the material is softened mechanically prior to its use as an absorbent material.

21 Claims, 4 Drawing Sheets

METHOD FOR THE MANUFACTURING OF AN ABSORBENT STRUCTURE AND AN ABSORBENT ARTICLE

BACKGROUND

1. Field of the Invention

The present invention relates to a method for manufacturing an absorbent structure in an absorbent article, such as a sanitary napkin, a tampon, a panty protector, an incontinence guard, a diaper, a wound or sore dressing, a saliva absorbent and like articles. The invention also relates to an article manufactured according to the method.

2. Discussion of Related Art

Many different types of absorbent articles of this kind are known to the art. The absorbent bodies of such articles are typically produced by dry-defibering and fluffing cellulose pulp in roll, bale or sheet form for instance, to form a pulp mat, sometimes admixed with so-called superabsorbent material in the pulp mat, these absorbents being polymers which are capable of absorbing many times their own weight of water or body fluid.

The pulp body is often compressed so as to enhance its fluid-wicking ability and also in order to reduce pulp body bulk and therewith obtain an article which is as compact as possible.

The absorbent body may also include other constituents, for instance constituents which will improve its fluid-aquisition properties or its fluid-retaining properties, or which will increase its coherent strength, i.e. its coherency, and its ability to withstand deformation in use.

One serious drawback with products of this nature is found in the total absorption capacity of the articles and also in the fact that the articles will often leak long before their total absorption capacity has been fully utilized. Among other things, this is because the body fluid discharged by the wearer is unable to penetrate into the absorption material and to spread to hitherto unused areas of the article quickly enough, but instead leaks from the sides of the sanitary napkin, the diaper or the incontinence guard. The ability of the materials used in the article to disperse the absorbed fluid throughout the entire absorbent body and to retain said fluid in the absorption body is thus highly important.

Another problem resides in so-called rewetting, i.e. the transference of body fluid that has already been absorbed back into contact with the wearer's skin as a result of external forces, for instance when the wearer sits down. It is generally desired that the surface of the article that lies proximal to the wearer in use will remain as dry as possible.

Another desideratum with regard to the majority of hygiene products is that the article shall be thin, so that it can be worn as discretely as possible.

A very large part of the production plants used in the manufacture of the aforesaid hygiene articles is comprised of defibrating equipment, pneumatic conveying systems and mat-forming equipment. This equipment is also the source of serious faults in the production plants. Equipment for compressing the finished pulp mat or the finished hygiene product is furthermore often included downstream of the production plants.

A separate problem is related to the use of superabsorbent material in absorbent articles. The superabsorbent material is normally available in the form of granules, which are difficult to bind to the absorbent structure especially if the percentage of superabsorbent is high, i e 50% and higher calculated on the total weight of the absorbent structure in a dry state.

It is known from International Patent Application WO 90/05808 to produce a pulp web by dry-forming, which is later defibered, so-called dry-formed roll or reel pulp. Flash-dried paper-pulp fibres, which may consist of thermomechanical pulp, chemi-thermomechanical pulp, CTMP, or chemical paper pulp, sulphite or sulphate pulp with a dry solids content of about 80% is delivered by means of an air stream in a controlled flow to a forming head arranged above a forming wire and there formed into a web that has a weight per unit area of 300–1500 g/m$^2$ and a density of 550–1000 kg/m$^3$. Air is sucked away through a suction box placed beneath the wire. The moisture content in the process shall be 5–30%.

The web is pre-pressed to a density of 550–1000 kg/m$^3$ in order to slightly reduce the bulk of the web prior to the final pressing stage. The pressed web has a mechanical strength which enables the web to be rolled-up or handled in sheet form for storage and transportation purposes. The web can be readily defibered and is intended to be converted into fluff for use in the manufacture of absorbent bodies or pads for diapers, sanitary napkins and like articles.

Another method for the manufacturing of an absorbent structure is described in European Patent 0 122 042, where a mixture of hydrophilic fibres and water insoluble particles of insoluble hydrogel is airlaid into a web and compressed to a density of 0.15 to about 1.0 g/cm3. This method however comprises several production steps, where the dry lap base material is first disintegrated into cellulose fibres by use of a hammer mill, whereafter the fibres are deposited on a screen surface and formed to the absorbent structure, which is then compressed. These manufacturing steps make this process rather complicated and expensive.

SUMMARY AND OBJECTS

An object of the present invention is to provide in an absorbent article of the aforedescribed kind an absorbent structure which exhibits extremely good absorption properties, especially with respect to its ability to spread fluid and also with respect to its ability to retain said fluid within the material. The material will preferably exhibit low rewetting tendencies as well as being capable of being made very thin. It is also desired to provide a simplified method of manufacturing absorbent articles of the kind defined in the introduction. These objects and desiderata are achieved with a manufacturing method in which particulate material comprising 30–100%, preferably at least 50% and most preferably at least 70% flash-dried cellulose fibres is dry-formed to a web with a weight per unit area of between 100–2000 g/m2 and compressed to a density of between 0.3–1.0 g/cm3 and that the web without subsequent defibration and fluffing is incorporated as an absorbent structure in an absorbent article.

Non-defibered, dry-formed roll pulp has been found to be an extremely good absorption material and can be used directly as an absorbent material in hygiene articles, without being defibered. The material also has good fluid wicking properties and swelling properties, which are meaningful to the function of the product. The pulp mat is very thin and therefore need not be further compressed in the product or article.

In the case of certain product applications in hygiene articles, it is convenient to soften dry-formed roll pulp prior to its use as an absorption material. The earlier mentioned good absorption properties, fluid wicking properties and swelling properties are not influenced by the softening process to any great extent. One method to soften an absorbent sheet is described in European Patent Application EP 0 360 472, where the compressed absorbent material is worked between partially cutting rollers and thereby gaining softness. This method however leads among other things to decreased strength in the softened material.

BRIEF DESCRIPTION OF THE DRAWINGS

The invention will now be described in more detail with reference to a number of exemplifying embodiments thereof and also with reference to the accompanying drawings, in which.

DETAILED DESCRIPTION OF THE PREFERRED EMBODIMENTS

Important properties of a material used in the manufacture of a hygiene article are its absorbent capacity, absorption rate, wicking capacity, drainage capacity, retention capacity, rewetting, softness and smoothness.

The fluids concerned are urine, menstruation blood, blood, fluid matter from wounds and sores, rinsing fluid and saliva.

An object of the present invention is to provide in an absorbent article such as a sanitary napkin, tampon, panty protector, incontinence guard, diaper, bed protector, wound or sore dressing, saliva absorbent and like articles, an absorbent structure which exhibits highly effective absorption properties, especially with regard to its fluid-wicking rate and its ability to retain fluid throughout the material. The material will also preferably have low rewetting and be capable of being made very thin and smooth. It is also desired to simplify the manufacturing process. A finished absorbent material in roll form which can be used without needing to be defibered would partially reduce the need for the earlier mentioned defibering equipment, pneumatic conveying systems and mat-forming equipment, and consequently there is a demand for such material.

The aforesaid objects and desiderata have been achieved in accordance with the invention by using a manufacturing method in which particulate material comprising 30–100%, preferably at least 50% and most preferably at least 70% flash-dried cellulose fibres is dry-formed to a web with a weight per unit area of between 100–2000 g/m2 and compressed to a density of between 0.3–1.0 g/cm3 and that the web without subsequent defibration and fluffing is incorporated as an absorbent structure in an absorbent article.

In accordance with the invention, there is used a dry-formed product which is manufactured from particulate material as mechanical pulp or chemi-thermomechanical pulp (CTMP) or a corresponding product manufactured from sulphite pulp or sulphate pulp, so-called chemical cellulose pulp. Cellulose fibres which have been stiffened chemically may also be used. In the dry-formed product can also be included other particulate matter as superabsorbents, thermoplastic binding fibres and other kind of fibres.

Non-treated dry-formed roll pulp has extremely good absorption, wicking and swelling properties, and it has been found possible to use the material immediately as an absorption material in hygiene articles without defibrating the pulp. In the case of certain absorbent articles, it has been found suitable to soften the material slightly prior to its use. One method of softening the material is described below.

Dry-formed roll pulp has a good integrity which means that in the case of use of superabsorbent materials in dry-formed roll pulp the granules will be well bound to the absorbent structure and will not spread during further conversion into absorbent hygiene products.

Dry-formed cellulose pulp can be produced, for instance, by forming a web of flash-dried paper pulp fibres in accordance with the method described in International Patent Application WO 90/05808.

Cellulose pulp fibres have a so-called curl value which defines the crookedness of the fibre. Curl value can be measured according to the method described by B. D. Jordan, N. G. Nguyen in Papper och Trä 4/1986, page 313. An embodiment of the present invention has a curl-value of between 0.20 and 0.40.

Softening of the Material

The material can be given a softness which renders the material highly suitable for use as an absorption material in the majority of hygiene articles, by working dry-formed roll pulp between for instance corrugated rolls. The material can be brought to different degrees of softness for different product applications, by working the material between different types of rolls and at different roll spacings.

Dry-formed roll pulp which has been softened in this way exhibits very good product properties, and the earlier mentioned good absorption properties are not influenced by the softening process to any great extent.

Figure 12:
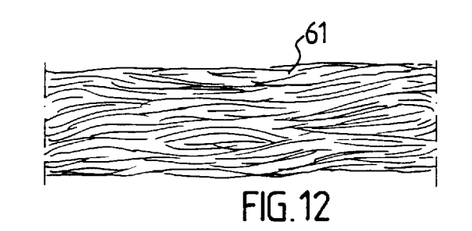
FIG. 12 illustrates the structure of a cross section of the material in unsoftened condition.
Figure 13:
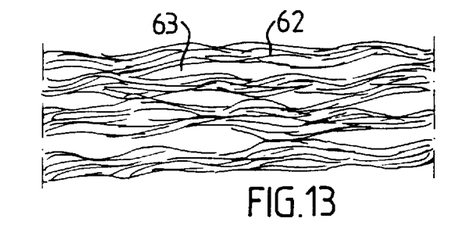
FIG. 13 illustrates the structure of a cross section of the material in softened condition.

The material is delaminated in the softening process as illustrated in FIGS. 12 and 13. The unsoftened material has normally an even high density throughout the whole the thickness of the material (61). As a result of the softening process the material is delaminated so as to form a plurality of partially separated (63), thin fibre layers (62). Softening and delamination of the material reduces its total density to some extent, although the original density is essentially retained in each individual layer. Because a very high density is retained in the individual layers, the good fluid wicking properties of the material are retained despite the increase in bulk obtained in conjunction with the softening process. The total bulk is increased by up to 300%, normally 1–100%, as a result of the softening process, depending on the method used and the extent to which the material is softened.

It will be understood that the aforesaid material softening method has been given solely by way of example and that corresponding results can be achieved with the aid of other methods. For instance, the material could eventually be softened by means of ultrasonic energy, microwaves, by moisturizing the material, or with the aid of chemical additives.

Investigation of Material Properties

The test equipment described below was used to evaluate absorption properties.

Method 1. Absorption Properties Up an Inclined Plane

A rectangular test body was punched from the material and a line was drawn transversely across the test body at a point 11 cm from one short end of the body. A fluid container was placed adjacent laboratory scales and both the scales and the container were adjusted to a horizontal position. A plexiglass plate was placed on the scales at a 30° slope, with one free edge of the plate extending slightly down into the container. A line had been drawn transversely across the plate at a point 11 cm from the lower edge of said plate. Test fluid (0.9% NaCl-solution) was poured into the container, until 20 mm of the plexiglass plate was located beneath the surface of the fluid. The test body was secured on the plexiglass plate so that the line drawn on the test body coincided with the line drawn on the plate while, at the same time, folding away the lower part of the test body so as to prevent it from coming into contact with the test liquid. A clock was started at the same time as the test body was laid onto the plate, with the test body extended down into the solution to the same extent as the plate. The increase in weight of the test body with time was recorded.

Method 2. Measurements of Absorption Capacity and Degree of Utilization

A test product was secured in a fixture. Test fluid (0.9% NaCl-solution) was delivered to the wetting point of the product over a period of 60 minutes at the rate at which the fluid was absorbed. The amount of fluid absorbed was measured continuously and the total amount of fluid absorbed by the product constitutes the utilized absorption capacity of the test product. The test product was then placed in a fluid bath, in which it had the maximum opportunity of absorbing test fluid. The test product was then again weighed and the total absorption capacity calculated. The degree of utilization is given by the quotient between the utilized absorption capacity of the test product and the total absorption capacity.

Method 3. Measurements of Rewetting, Fluid Wicking and Aquisition Time

Four batches of sample fluid (0.9% NaCl-solution), each comprising 28 ml, were delivered at 20-minute intervals. The time measurement was continued until all fluid had been absorbed. The extent to which the fluid had dispersed in the diaper was noted after each batch. Subsequent to delivering the last batch of fluid, filter paper was placed over the wetting point and loaded with a weight of 1.1 kg for 15 seconds. The filter paper was weighed both before and after applying the load and rewetting was recorded.

Method 4. Determining Rewetting Measurements

A diaper intended for a given weight range was weighed and then placed on a flat support surface. An adapted quantity of test fluid (0.9% NaCl-solution, 100 ml for a diaper intended for a weight range of 7–15 kg) was delivered to the wetting point of the diaper. A further 100 ml of fluid was delivered after 20 minutes. When all fluid had been absorbed, a filter paper was placed over the wetting point and loaded with a weight of 1.1 kg for 15 seconds. The filter paper was weighed both before and after applying the load and the result was recorded as a first rewetting instance. After a further 20 minutes, another 100 ml of fluid was delivered and when all fluid had been absorbed, the procedure was repeated with a fresh filter paper and the result recorded as a second rewetting instance.

Method 5. Determining Blood Absorption

A test body, 65×200 mm, was punched from the material. 5 ml test fluid (0.9% NaCl-solution) were delivered to the wetting point on the test body. Dispersion of the fluid was measured after about 30 minutes. A further 5 ml of test fluid (0.9% NaCl-solution) were then delivered to the wetting point and fluid dispersion was measured after about a further 30 minutes. Subsequent to the last delivery, eight filter papers were placed over the wetting point and loaded with a weight of 4.875 kg for 15 seconds. The filter papers were weighed both before and after applying the load and rewetting was recorded.

Test Results

Softening

Figure 1:
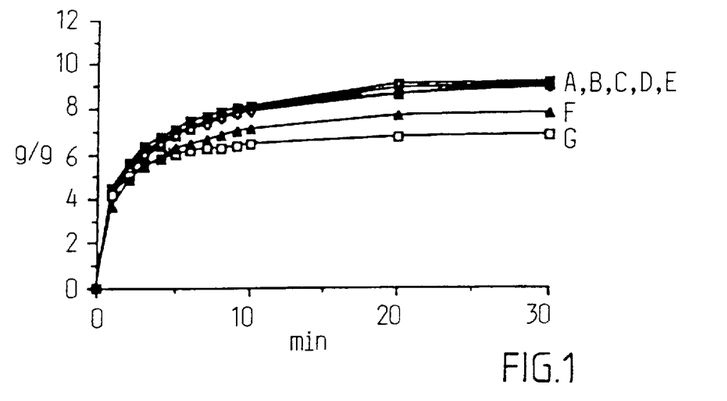
FIG. 1 illustrates the absorption properties of a dry-formed CTMP-material subsequent to being worked between rolls at different roll spacings. Conventionally formed and compressed pulp mats of CTMP-pulp and chemical pulp respectively were used as references.

With the intention of investigating how the material was affected at different softening roll spacings when softening the material, a material was tested under different softening conditions. For instance, in the case of a dry-formed CTMP-material having a weight per unit area of 900 g/m$^2$ and a density of 0.63 g/cm$^3$, a suitable roll spacing is 1.7–2.4 mm during the softening process. The material is not influenced to any great extent at roll spacings which lie within this range. FIG. 1 illustrates the absorption properties at different roll spacings. The results were determined in accordance with Method 1.

A Material according to the invention, roll spacing 1.7 mm.

B Material according to the invention, roll spacing 2.0 mm.

C Material according to the invention, roll spacing 2.4 mm.

D Material according to the invention, roll spacing 2.0 mm, softened twice.

E Material according to the invention, roll spacing 2.0 mm, softened four times.

F CTMP-pulp, density 0.125 g/cm$^3$.

G Chemical sulphate pulp, density 0.125 g/cm$^3$.

Absorption Properties of Absorbent Structures

Figure 2:
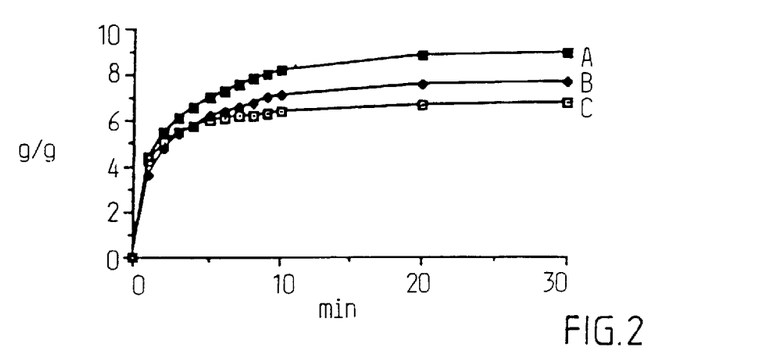
FIG. 2 illustrates the absorption properties of a dry-formed CTMP-material subsequent to being softened. Conventionally formed and compressed mats comprised of CTMP-pulp and chemical pulp respectively were used as references.

The absorption properties of an inventive CTMP-material having a weight per unit area of 900 g/m$^2$ and a density of 0.63 g/cm³ compared with those of corresponding pulp cores produced from conventionally defibred and web-formed CTMP and corresponding chemical pulp are shown in FIG. 2. In the absence of superabsorbent material, the absorption capacity is about 9 g of fluid for each gram of absorbent material. The results were determined in accordance with Method 1.

A Material according to the invention.

B CTMP-pulp, density 0.125 g/cm³.

C Chemical sulphate pulp, density 0.125 g/cm³.

Product Properties of a Complete Absorbent Article

With the intention of studying other properties of complete absorbent articles, test products were prepared in the form of conventional children's diapers which comprised a T-shaped absorbent body (T-core), which lies nearest the wearer, and a rectangular absorbent body (R-core) which lies beneath the T-core, where the rectangular absorbent body in the test products was produced from an inventive CTMP-material. In the conventional products, the T-shaped absorbent body (T-core) and the rectangular absorbent body (R-core) were comprised of conventional defibred CTMP and chemical pulp.

Measurements of the Absorption Capacity

Products which comprised an inventive CTMP-material exhibited an absorption in grams which was equivalent to the reference products which had corresponding pulp cores that were comprised of conventionally defibred and mat-formed CTMP and chemical pulp. The results are set forth in FIG. 3. The results were determined in accordance with Method 2.

Figure 3:
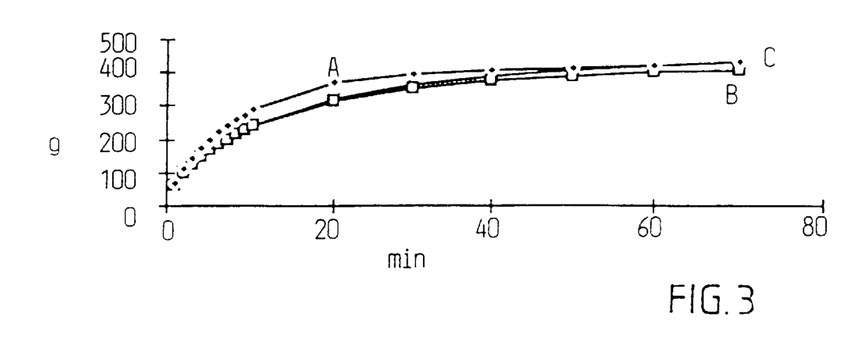
FIG. 3 illustrates the absorption properties of a complete absorbent article manufactured with dry-formed CTMP in the core. Conventionally manufactured products of corresponding compositions were used as references.

A Reference diaper Libero Girl.

B Reference diaper Libero Boy.

C Child diaper comprising inventive material.

Measurements of Fluid Aquisition Time

Products in which the R-core comprised an inventive CTMP-material exhibited a shorter fluid aquisition time than the reference product. This implies that an R-core which contains inventive CTMP-material is able to drain the T-core more effectively. The results can be seen from FIG. 4. The results were determined in accordance with Method 3.

Figure 4:
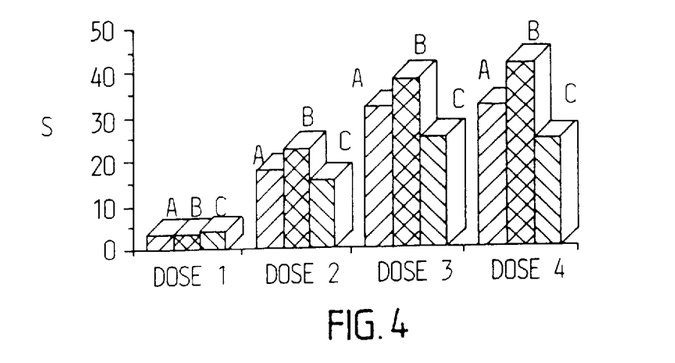
FIG. 4 illustrates the fluid aquisition time of a complete absorbent article produced with dry-formed CTMP in the core. Conventionally manufactured products of corresponding compositions were used as references.

A Reference diaper Libero Girl.

B Reference diaper Libero Boy.

C Child diaper comprising inventive material.

Measurements of the Utilization of the Absorbent Body

A comparison between the degree of utilization of the absorbent body in an absorbent article which contained an inventive CTMP-material and a corresponding absorbent article which contained conventional CTMP and chemical pulp showed that the degree of utilization is about the same, although slightly on the plus side for an inventive CTMP-material. The results can be seen from FIG. 5. The results were determined in accordance with Method 2.

Figure 5:
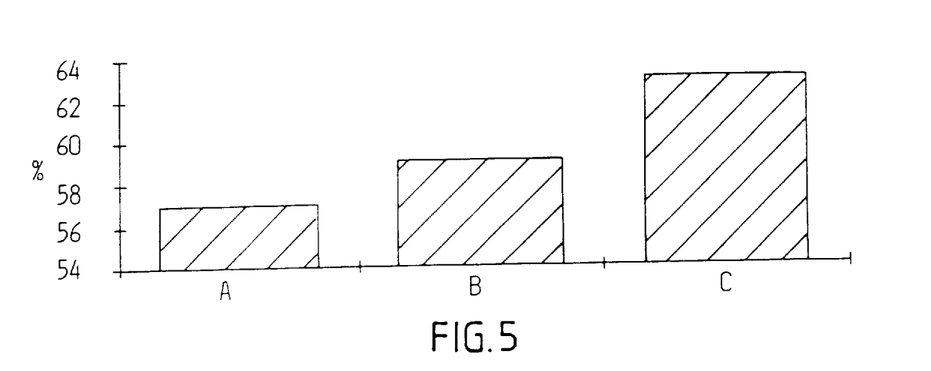
FIG. 5 illustrates the degree of utilization of a complete absorbent article produced with dry-formed CTMP in the core. Conventionally manufactured products of corresponding compositions were used as references.

A Reference diaper Libero Girl.

B Reference diaper Libero Boy.

C Child diaper comprising inventive material.

Admixing Superabsorbent Material

Figure 6:
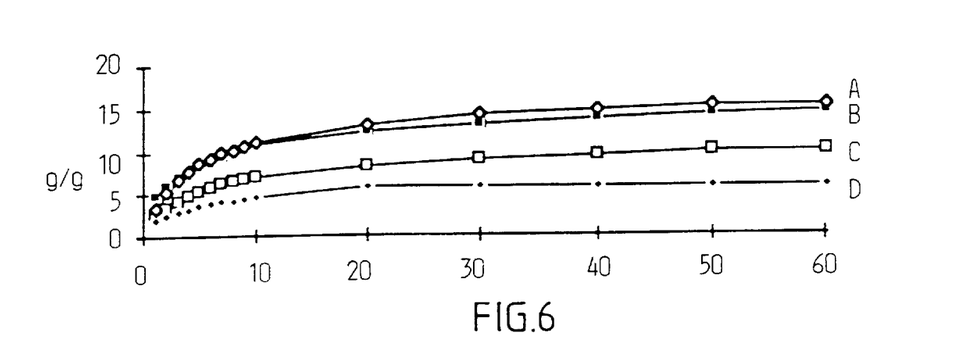
FIG. 6 illustrates the absorption properties of an absorbent structure produced with dry-formed CTMP, both with and without a superabsorbent admixture. Conventionally manufactured pulp cores both with and without a superabsorbent admixture were used as references.

The presence of superabsorbent material in an absorbent body will influence the absorption properties of the body. Superabsorbent material can be incorporated in the absorbent body in different ways. For instance it may be admixed with the body material, laid in layers in the body, or disposed therein in some other way. This admixture of superabsorbent material can be effected in conjunction with manufacturing the dry-formed material, although it may also be effected during some other part of the manufacturing process. The absorption properties were compared with an inventive CTMP-material to which no superabsorbent material had been added and also with corresponding pulp cores comprised of conventional defibred CTMP and chemical pulp. The results of this comparison are shown in FIG. 6. The results were determined in accordance with Method 1.

A Chemical sulphate pulp containing 30% superabsorbent and having a density of 0.125 g/cm³.

B Inventive material containing 30% superabsorbent.

C Reference diaper containing 30% superabsorbent.

D Inventive material containing no superabsorbent.

Rewetting Measurements

Products which comprised an inventive CTMP-material in the R-core exhibited better rewetting values than the reference product. This also implies that an R-core which contains inventive CTMP-material is able to drain the T-core more effectively. The results can be seen from FIG. 7. The results were determined in accordance with Method 4.

Figure 7:
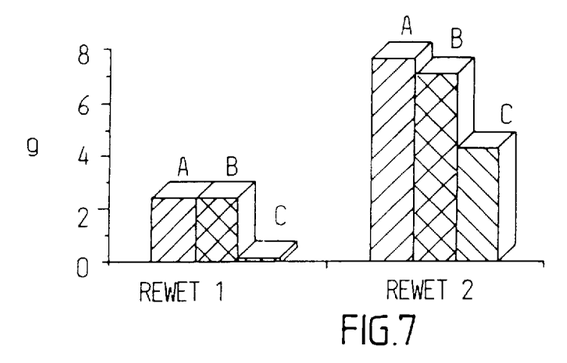
FIG. 7 illustrates rewetting of a complete absorbent article produced with dry-formed CTMP in the core. Conventionally manufactured products of corresponding compositions were used as references.

A Reference diaper Libero Girl.

B Reference diaper Libero Boy.

C Child diaper comprising inventive material.

Rewetting Measurements, Specific for Blood Absorption

In the case of blood absorption, products which comprised an inventive softened CTMP-material showed better rewetting values than non-softened products. The results also showed that when absorbing blood, products which lacked superabsorbent material exhibited lower rewetting values than material which contained superabsorbent material. Material which lacks superabsorbent material also disperses blood much more effectively. The results can be seen from FIGS. 8 and 9. The reference products comprised two different products frequently found on the market. The results were determined in accordance with Method 5. The prerequisites for this effect are that at least one layer of the pulp mat is free from superabsorbent material. Of course, this does not exclude the presence of such material in other parts of the absorbent article.

Figure 8:
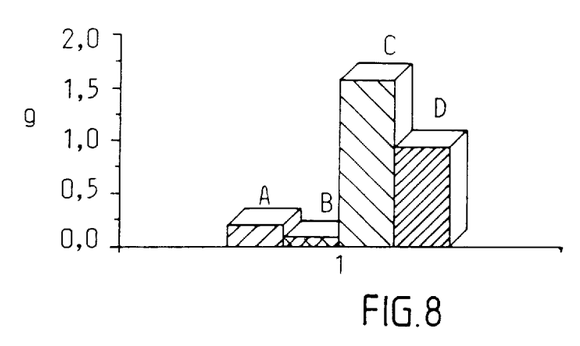
FIG. 8 illustrates the respective rewetting of an unsoftened and a softened absorbent structure in connection with blood absorption which was produced with dry-formed CTMP in the core, both with and with-out a superabsorbent admixture.

FIG. 8

A Inventive material 350 g/m2.

B Inventive material 350 g/m2, softened.

C Inventive material 350 g/m2+5% superabsorbent.

D Inventive material 350 g/m2+5% superabsorbent, softened.

Figure 9:
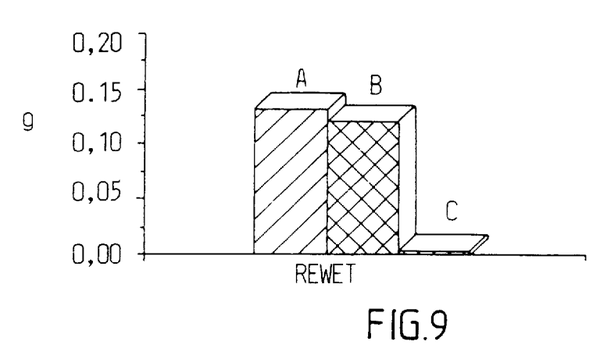
FIG. 9 illustrates rewetting of a completely absorbent article in connection with blood absorption which was produced from dry-formed CTMP in the core. Conventionally manufactured products of corresponding composition were used as references.

FIG. 9

A Reference product 1.

B Reference product 2.

C Product containing inventive material.

Network Strength

Dry-formed roll pulp will normally have sufficient mat strength for the product applications intended here. If the network strength of certain product applications should be found insufficient, the network strength can be increased by reinforcing the structure in some suitable manner, by adding reinforcing fibres, binding fibres or binding agent to the cellulose fibre mixture. The network strength can also be increased by incorporating a reinforcing layer of, for instance, plastic, non-woven, net or threads in the absorbent structure, or by fastening a reinforcing layer or an outer sheet on one or both sides of the material.

Density and Surface Weight

The softened pulp mat is still very thin, and consequently it is unnecessary in many cases to further compress the mat prior to its use in an absorbent article. A suitable density is 0.3–1.0 g/cm³, preferably 0.4–0.9 g/cm³ and most preferably 0.5–0.85 g/cm³. A suitable weight per unit area is between 100–2000 g/m², preferably 150–1500 g/m² and most preferably 200–1000 g/cm². When calculating the density, the thickness of the material was measured with the aid of a Mitutoyo thickness meter.

Description of a First Exemplifying Embodiment

Figure 10:
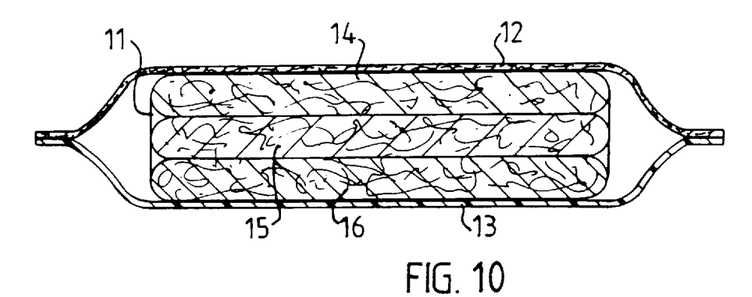
FIGS. 10–11 illustrate schematically the composition of various exemplifying embodiments of inventive absorbent articles.

FIG. 10 illustrates a diaper constructed in accordance with one embodiment of the invention. The diaper includes, in a conventional manner, an absorbent body 11 which is enclosed between a fluid-permeable top sheet 12, which conveniently comprises a soft non-woven material, a perforated plastic film or the like and which is intended to lie proximal to the wearer in use, and a fluid-impermeable bottom sheet 13. The sheets 12 and 13 have parts which extend beyond the absorbent body 11 and the sheets are joined together at these protruding parts. The bottom sheet 13 is comprised of a suitable plastic material, for instance polyethylene. It will be understood, however, that other known materials can be used for the top and bottom sheets, within the scope of the invention.

The absorbent body is comprised of two or more layers, an upper fluid aquisition layer 14 and one or two lower wicking layers and storage layers 15 and 16. The inventive material is used either as a wicking layer 15 or a storage layer 16 or as both these layers. Those layers in which inventive material is not used may be comprised of other types materials, for instance conventional cellulose fibre material.

The purpose of the aquisition layer 14 is to rapidly take-up a given quantity of fluid. This fluid shall solely be held loosely in the fibre structure and quickly drained therefrom. The aquisition layer 14 has a relatively open fibre structure of relatively low density and contains 0–10% superabsorbent material. The superabsorbent material used in the aquisition layer 14 will preferably have a high gel strength, so that an open three-dimensional fibre structure will be retained in this layer after becoming wet.

The main purpose of the wicking layer 15 is to transport the fluid received in the aquisition layer 14 effectively to the storage layer 16 located beneath the wicking layer 15 and to ensure that the greatest possible part of the storage layer 16 is utilized for absorption purposes. The wicking layer 15 therefore has a relatively low superabsorbent content. A suitable superabsorbent content in the case of the wicking layer 15 is 0–20%, while a suitable density range is 0.3–1.0 g/cm3. A suitable weight per unit area range in the case of the wicking layer 15 is 50–1500 g/m2.

The purpose of the storage layer 16 is to absorb and retain the fluid which is dispersed to the storage layer 16 through the wicking layer 15. The storage layer 16 may therefore have a relatively high superabsorbent content and a relatively high density. Suitable density values are 0.4–1.0 g/cm3, while a suitable superabsorbent content is 30–70%. A suitable weight per unit area range in the case of the storage layer 16 is 100–1500 g/m2.

The wicking layer 15 and the storage layer 16 may optionally be combined to form a single layer. In this case, the single layer will have a relatively high superabsorbent content and a relatively high density. Suitable density values are 0.3–1.0 g/cm3, while a suitable superabsorbent content is 20–70%. A suitable weight per unit area range in the case of a combined wicking and storage layer is 150–2000 g/m2.

When the wicking layer 15 and the storage layer 16 are combined in a single layer, the superabsorbent content of the layer can be varied throughout the product, so as to obtain a superabsorbent gradient in the depth, length and/or the breadth direction of the product.

The various layers may have different forms and sizes. Normally, the absorbent structure is combined with some form of elastication, inter alia in the crotch region of the product, in order to improve product efficiency.

Destination of a Second Exemplifying Embodiment

Figure 11:
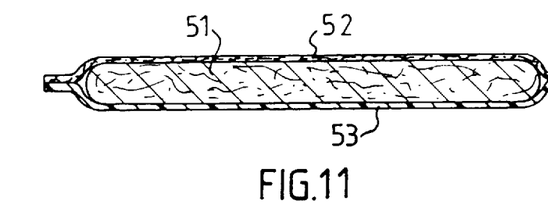

FIG. 11 illustrates an exemplifying embodiment of an inventive saliva absorbent. The saliva absorbent includes, in a conventional manner, an absorbent body 51 which is enclosed between a fluid-permeable top sheet 52, which is suitably comprised of a perforated plastic film or like material and which is intended to lie proximal to the wearer when used, and a fluid-impermeable bottom sheet 53. The bottom sheet 53 is comprised of a suitable plastic material, for instance polyethylene. It will be understood, however, that the top sheet 52 and the bottom sheet 53 may be comprised of other known materials within the scope of the invention.

The absorbent body 51 is comprised solely of one single layer. This layer may be comprised of inventive dry-formed material and has a relatively high density and a superabsorbent content of 20–80%. A suitable density range in respect of the absorbent body 51 is 0.4–0.8 g/cm3.

It will be understood that the invention is not restricted to the illustrated and described exemplifying embodiments thereof and that other embodiments are conceivable within the scope of the following Claims.

We claim:

1. The use, in absorbent structures incorporated in absorbent articles, such as diapers, sanitary napkins, tampons, panty protectors, incontinence guards, bed protectors, wound or sore dressings, saliva absorbents and like articles, of a web dry-formed of particulate material containing 30–100% flash-dried cellulose fibres to a web with a weight per unit area of 100–2000 g/m², compressed to a density of 0.3–1.0 g/cm³, and mechanically softened and delaminated before incorporation as the absorbent structure without any subsequent defibration and fluffing.

2. A method for manufacturing an absorbent structure in an absorbent article, comprising:

flash drying paper pulp into flash-dried cellulose fibers, dry-forming particulate material to a web with a weight per unit area of between 100–2000 g/m², 30–100% of the particulate material including the flash-dried cellulose fibers, compressing said web to a web density of between 0.3–1.0 g/cm³, mechanically softening and delaminating the web, and incorporating said mechanically softened and delaminated web as an absorbent structure in an absorbent article without subsequent defibration and fluffing.

3. The method for manufacturing an absorbent structure according to claim 2, comprising compressing said web to a web density of between 0.4–0.9 g/cm³.

4. The method for manufacturing an absorbent structure according to claim 2, wherein the step of softening and therewith delaminiating said web before incorporating it as an absorbent structure in an absorbent article achieves in said web a plurality of partially separated thin fibre layers, which in themselves exhibit a density which corresponds to said web density.

5. The method of claim 2, wherein the absorbent article is a diaper, sanitary napkin, panty protector, incontinence guard, bed protector, a wound or sore dressing, or saliva absorbent.

6. An absorbent structure, wherein the structure has been manufactured according to the method claimed in claim 2.

7. The absorbent structure according to claim 6, wherein the weight per unit area of the structure is between 150–1500 g/m².

8. The absorbent structure according to claim 6, wherein said cellulose fibres are mainly comprised of fibres of chemi-thermomechanically produced pulp.

9. The absorbent structure according to claim 8, wherein said chemi-thermomechanical pulp fibres have a curl value of between 0.20 and 0.40.

10. The absorbent structure according to claim 6, wherein said cellulose fibre are mainly comprised of fibres of chemically produced pulp.

11. The absorbent structure according to claim 6, wherein some of said fibres are chemically stiffened cellulose fibres.

12. The absorbent structure according to claim 6, wherein the structure includes between 20–70% superabsorbent material, calculated on the total weight of the structure in a dry state.

13. The absorbent structure according claim 6, wherein the structure includes reinforcing means.

14. The absorbent structure of claim 6, wherein the absorbent article is a diaper, sanitary napkin, panty protector, incontinence guard, bed protector, a wound or sore dressing, or saliva absorbent.

15. The absorbent structure of claim 13, wherein the reinforcing means is a binding agent, reinforcing fibers, or thermoplastic binding fibers.

16. An absorbent article, comprising a liquid-permeable top sheet, an essentially liquid-impermeable bottom sheet, and an absorbent body which includes an absorbent structure according to claim 6 enclosed between said sheets.

17. The absorbent article according to claim 16, wherein said absorbent body includes at least two layers, an acquisition layer and a second layer, said acquisition layer includes means for taking up fluid and delivering the fluid to said second layer, said acquisition layer including the absorbent structure having a weight per unit area of between 100–1500 g/m$^2$ and a density of between 0.3–1/0 g/cm$^3$, wherein said second layer is one of a wicking layer and a storage layer.

18. The absorbent article according to claim 17, wherein said wicking layer includes between 0–40% superabsorbent material calculated on the total weight of the structure in a dry state.

19. An absorbent article according to claim 16, wherein said absorbent body includes two layers, an acquisition layer and a storage layer wherein said acquisition layer includes means for quickly taking up fluid and delivering the fluid to said storage layer, said storage layer comprising the absorbent structure having a weight per unit area of between 100–2000 g/m$^2$ and a density of between 0.4–1.0 g/cm$^3$.

20. The absorbent article according to claim 19, wherein said storage layer includes between 20–70% superabsorbent material calculated on the total weight of said structure in a dry state.

21. The absorbent article of claim 16, wherein the absorbent article is a diaper, sanitary napkin, panty protector, incontinence guard, bed protector, a wound or sore dressing, or saliva absorbent.

* * * * *